United States Patent [19]

Croizy et al.

[11] Patent Number: 5,585,514

[45] Date of Patent: Dec. 17, 1996

[54] PROCESS FOR THE MANUFACTURE OF BIACETYL-FREE METHYL METHACRYLATE

[75] Inventors: Jean-François Croizy, Farschviller; Marc Esch, Freyming-Merlebach, both of France

[73] Assignee: Elf Atochem S.A., Puteaux, France

[21] Appl. No.: 464,223

[22] Filed: Jun. 5, 1995

[30] Foreign Application Priority Data

Jun. 30, 1994 [FR] France .................................. 94 08103

[51] Int. Cl.$^6$ .................................................. C07C 67/48
[52] U.S. Cl. .................................................. 560/218
[58] Field of Search ............................................. 560/218

[56] References Cited

U.S. PATENT DOCUMENTS

| 4,304,925 | 12/1981 | Watanabe et al. | 560/218 |
| 4,668,818 | 5/1987 | Lipp et al. | 560/215 |
| 5,468,899 | 11/1995 | Bauer et al. | 560/218 |

FOREIGN PATENT DOCUMENTS 343583  11/1989  European Pat. Off. .

Primary Examiner—Paul J. Killos
Attorney, Agent, or Firm—Millen, White, Zelano, & Branigan, P.C.

[57] ABSTRACT

A process for producing methyl methacrylate comprises: (a) reacting acetone cyanohydrin with sulphuric acid or an oleum, in order to obtain methacrylamide; (b) reacting the methacrylamide thus obtained either directly, or after it has been isolated, with methanol in the presence of water; (c) separating the methyl methacrylate from the sulphuric acid, ammonium sulphate and water mixture by distillation; (d) removing the unreacted methanol by liquid-liquid extraction; (e) distilling the washed methyl methacrylate in two stages: (e1) firstly, in order to remove the remaining traces of water, of methanol and of low-boiling-point impurities; then (e2) in order to separate the pure methyl methacrylate from the high- boiling-point impurities. An improved purification step comprises conducting, step (e) in the presence of at least one non-aromatic 1,2-diamine which is capable of reacting, under acid catalysis, with the biacetyl present as impurity in the methyl methacrylate and of reducing the content thereof, the said non-aromatic 1,2-diamine being introduced at a point such that its contact time with the methyl methacrylate is sufficient for it to be able to react substantially with the biacetyl present.

12 Claims, No Drawings

PROCESS FOR THE MANUFACTURE OF BIACETYL-FREE METHYL METHACRYLATE

BACKGROUND OF THE INVENTION

The present invention relates to a process for the separation of diacetyl from methyl methacrylate, which separation has particular value in the manufacture of monomeric methyl methacrylate by reaction of acetone cyanohydrin with sulphuric acid in order to form methacrylamide, which is then esterified with methanol.

With such a manufacturing process, the monomeric methyl methacrylate is obtained with about 1 to 5 ppm of biacetyl (2,3-butanedione) as impurity responsible for the yellowing of the poly(methyl methacrylate). In order to avoid this problem of yellowing of the polymer formed, the process must be performed such that the biacetyl content in the monomeric methyl methacrylate is less than 0.1 ppm.

In accordance with European patent EP-B-0,206,230, it is proposed to add to the esterification reaction mixture an effective amount of an aromatic ortho-diamine, such as ortho-phenylenediamine, in the presence of an acid catalyst (for example sulphuric acid), which is present in an amount of 0.1 to 65% by weight of the reaction mixture. The aromatic orthodiamine may also be added after separation of the finished monomer, with addition of a suitable amount of inorganic acid.

Such a process allows for satisfactory removal of the biacetyl; however, it has the drawbacks of having to use aromatic ortho-diamines which are expensive and toxic compounds and which may result in a decrease in the stability of the monomeric methyl methacrylate, on account of the presence in the latter of the product of reaction of the biacetyl and the aromatic ortho-diamine. This may lead to frequent encrustation of the distillation column heating pipes.

SUMMARY OF THE INVENTION

An object of the invention, therefore is to provide a more satisfactory solution for the removal of the biacetyl in monomeric methyl methacrylate.

Upon further study of the specification and appended claims, further objects and advantages of this invention will become apparent to those skilled in the art.

It has now been discovered, surprisingly, that the use of a non-aromatic 1,2-diamine especially ethylene diamine or cis-diaminocyclohexane make it possible to achieve these objectives.

Thus, there is provided by the present invention in the purification of impure methyl methacrylate containing impurities comprising biacetyl, the improvement comprising adding at least one non-aromatic 1,2-diamine to the impure methyl methacrylate so as to react the biacetyl with non-aromatic 2,3-diamine to form a reaction product, and separating the resultant reaction product from the methyl methacrylate, said non-aromatic 1,2-diamine being selected from the group consisting of ethylene diamine and cis-diaminocyclohexane.

A more comprehensive aspect of the present invention is directed to a process for the manufacture of monomeric methyl meth-acrylate, comprising the steps consisting in:

(a) reacting acetone cyanohydrin with sulphuric acid or an oleum, in order to obtain methacrylamide;

(b) reacting the methacrylamide thus obtained either directly, or after it has been isolated, with methanol in the presence of water;

(c) separating the methyl methacrylate from the sulphuric acid, ammonium sulphate and water mixture by distillation;

(d) removing the unreacted methanol by liquid—liquid extraction;

(e) distilling the washed methyl methacrylate in two stages:

(e1) firstly, in order to remove the remaining traces of water, of methanol and of low boiling-point impurities; then (e2) in order to separate the pure methyl methacrylate from the high-boiling-point impurities, wherein step (e) is carried out in the presence of at least one of said non-aromatic 1,2-diamines which is capable of reacting, under acid catalysis, with the biacetyl present as impurity in the methyl methacrylate and of reducing the content thereof, the said nonaromatic 1,2-diamine being introduced at a point such that its contact time with the methyl methacrylate is sufficient for it to be able to react substantially with the biacetyl present.

The reaction of biacetyl with the non-aromatic 1,2-diamine is catalysed by an acid, this being the methacrylic acid present in the medium in high proportion (1 to 2% by weight) relative to the biacetyl (a few ppm). Similarly, a few traces of sulphuric acid in the medium cannot be excluded. The contact time between the non-aromatic 1,2-diamine and the methyl methacrylate to be distilled is generally at least 10 minutes. It is preferably from 10 to 30 minutes.

Moreover, the non-aromatic 1,2-diamine is introduced in an amount of 1 to 200 mol, preferably in an amount of at least 10 mol, per mole of biacetyl present in the methyl methacrylate to be distilled.

The non-aromatic 1,2-diamine is preferably introduced into the feed for the distillation column of step (e1), the distillation being carried out continuously or discontinuously.

The distillation of step (e1) is generally carried out at reduced pressure (for example at a pressure of the order of 0.4 bar). As regards the distillation of step (e2), it is generally also carried out at reduced pressure (for example at a pressure of about 0.1 to 0.4 bar).

Step (e) is, moreover, advantageously carried out in the presence of at least one polymerization inhibitor, which is chosen in particular from phenothiazine, ditert-butylcatechol, hydroquinone methyl ether, hydroquinone and mixtures thereof.

The process in accordance with the present invention makes it possible to obtain a methyl meth-acrylate having a final biacetyl content of less than 0.1 ppm (detection threshold of the analysis method used).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding French application 94/08103, are hereby incorporated by reference.

EXAMPLE 1 (DISCONTINUOUS DISTILLATION)

Methyl methacrylate containing 4.5 ppm of biacetyl, derived from step (e1) of a process in accordance with the present invention, is introduced into a distillation column.

5 ppm of ethylenediamine are introduced into the heating pipe. The distillation is carried out at 400 mbar for about 2 hours. Methyl methacrylate is recovered at the column head, the biacetyl content in which product is measured by W assay of the quinoxaline obtained by reaction of the remaining biacetyl with ortho-phenylenediamine added in excess in acidic medium.

As a result, a methyl methacrylate containing only 0.1 ppm of biacetyl is obtained.

EXAMPLE 2 (CONTINUOUS DESTINATION)—STEP (E2)

Methyl methacrylate containing 2.3 ppm of biacetyl, derived from step (e1) of a process in accordance with the present invention, in an amount of 300 cm$^3$/h, and a solution of 1,2-ethylenediamine in pure methyl methacrylate, in an amount of 10 cm$^3$/h, are introduced into a vessel of adjustable volume, mounted just before the feed of a distillation column and maintained at a temperature of about 75° C. The concentration of 1,2-ethylenediamine is adjusted as a function of the desired molar ratio between the 1,2-ethylenediamine and the biacetyl. In this case, this ratio is 20.

After a residence time of 10 minutes in this vessel, the mixture is introduced in the middle of the distillation column and a distillation is carried out at a pressure of 500 mbar, with a heating pipe temperature of 81° to 83° C. and a column head temperature of 54°–55° C.

Pure methyl methacrylate and heavy products are recovered, in a weight ratio of 88–90/12–10. The heavy products contain 1,2-ethylenediamine and the pyrazine formed.

The methyl methacrylate thus purified contains less than 0.1 ppm of biacetyl.

EXAMPLES 3 to 7—STEP (e2)

Example 2 is repeated, modifying the residence time in the adjustable-volume capacity and the 1,2-ethylenediamine/-biacetyl molar ratio, as indicated in the Table below.

The results are also reported in the Table below.

These Examples, carried out on a methyl meth-acrylate derived from step (e1), simulate a placing in contact of the biacetyl with the 1,2-ethylenediamine of a methyl methacrylate derived from step (d), since there is a residence time in the heating pipe of step (e1).

TABLE

| Example | Residence time (minutes) | 1,2-Ethylene-diamine/biacetyl molar ratio | Residual biacetyl (ppm) | Yield for removal of the biacetyl (%) |
| --- | --- | --- | --- | --- |
| 2 | 10 | 20 | <0.1 | >95 |
| 3 | 10 | 25 | <0.1 | >95 |
| 4 | 10 | 50 | <0.1 | >95 |
| 5 | 20 | 20 | <0.1 | >95 |
| 6 | 20 | 50 | <0.1 | >95 |
| 7 | 30 | 50 | <0.1 | >95 |

EXAMPLE 8—STEP (e1)

Methyl methacrylate containing 3.5 ppm of biacetyl, derived from step (d) of a process in accordance with the present invention, in an amount of 300 cm$^3$/h, and a solution of 1,2-ethylenediamine in pure methyl methacrylate, in an amount of 10 cm$^3$/ht are introduced in mid-column into a continuous-distillation column. The concentration of 1,2-ethylenediamine is adjusted as a function of the desired molar ratio between the 1,2-ethylenediamine and the biacetyl. In this case, this ratio is 200.

The distillation is carried out at a pressure of 500 mbar, with a heating pipe temperature of 81° C. and a column head temperature of 45° C.

Methyl methacrylate and the heavy products are recovered from the foot of the column; water and light products in an 89.4/10.6 weight ratio are recovered at the head of the column. After separation of the methyl methacrylate and the heavy products (step (e2)), the heavy products contain the 1,2-ethylenediamine and the pyrazine formed.

The methyl methacrylate thus purified contains less than 0.1 ppm of biacetyl. Successive tests were performed without cleaning the device used. At the end of the treatment, lasting approximately 240 hours in total, no encrustation of the heating pipe was observed visually.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the manufacture of monomeric methyl methacrylate, comprising:
   (a) reacting acetone cyanohydrin with sulphuric acid or an oleum, in order to obtain methacrylamide;
   (b) reacting the methacrylamide thus obtained either directly, or after it has been isolated, with methanol in the presence of water;
   (c) separating the methyl methacrylate from the sulphuric acid, ammonium sulphate and water mixture by distillation;
   (d) removing the unreacted methanol by liquid—liquid extraction;
   (e) distilling the washed methyl methacrylate in two stages:
      (e1) firstly, in order to remove the remaining traces of water, of methanol and of low boiling-point impurities; then
      (e2) in order to separate the pure methyl methacrylate from the high-boiling-point impurities, the improvement comprising conducting step (e) in the presence of at least one non-aromatic 1,2-diamine which is capable of reacting, under acid catalysis, with the biacetyl present as impurity in the methyl methacrylate and of reducing the content thereof, said non-aromatic 1,2-diamine being introduced at a point such that its contact time with the methyl methacrylate is sufficient for it to be able to react substantially with the biacetyl present, said non-aromatic 1,2-diamine being selected from the group consisting of ethylenediamine and cis-diaminocyclohexane.

2. A process according to claim 1, wherein ethylenediamine or is used as the non-aromatic 1,2-diamine.

3. A process according to claim 1, wherein the contact time between the non-aromatic 1,2-diamine and the methyl methacrylate to be distilled is at least 10 minutes.

4. A process according to claim 1, wherein the non-aromatic 1,2-diamine is introduced in an amount of 1 to 200 mol per mole of biacetyl present in the methyl methacrylate to be distilled.

5. A process according to claim 4, wherein the non-aromatic 1,2-diamine is introduced in an amount of at least 10 mol per mol of biacetyl present in the methyl methacrylate to be distilled.

6. A process wherein the non-aromatic 1,2-diamine is introduced into the feed of the distillation column of step (e1), the distillation being carried out continuously or discontinuously.

7. A process according to claim 6, wherein the distillation of step (e1) is carried out at reduced pressure.

8. A process according to claim 7, wherein the distillation of step (e2) is carried out at reduced pressure.

9. A process according to claim 1, wherein step (e) is carried out in the presence of at least one polymerization inhibitor selected from the group consisting of di-tert-butylcatechol, hydroquinone methyl ether, and hydroquinone.

10. A process according to claim 1, wherein the methyl methacrylate product from (e2) has a final biacetyl content of less than 0.1 ppm.

11. In the purification of impure methyl methacrylate containing impurities comprising biacetyl, the improvement comprising adding at least one non-aromatic 1,2-diamine to the impure methyl methacrylate so as to react the biacetyl with said non-aromatic 1,2-diamine to form a reaction product, and separating the resultant reaction product from the methyl methacrylate, said non-aromatic 1,2-diamine being selected from the group consisting of ethylene diamine and cis-diaminocyclohexane.

12. A process according to claim 11, wherein the non-aromatic 1,2-diamine is ethylene diamine.

* * * * *